(12) United States Patent
Maeda et al.

(10) Patent No.: US 6,447,471 B1
(45) Date of Patent: Sep. 10, 2002

(54) BLOOD CIRCUIT DETACHING APPARATUS

(75) Inventors: Teiryo Maeda; Shigeru Otsuka, both of Kanagawa; Tomomichi Ego, Shizuoka, all of (JP)

(73) Assignee: Maeda Insitute of Renal Research, Kanagawa (JP)

( * ) Notice: Subject to any disclaimer, the term of this patent is extended or adjusted under 35 U.S.C. 154(b) by 0 days.

(21) Appl. No.: 09/321,577

(22) Filed: May 28, 1999

(30) Foreign Application Priority Data

May 29, 1998 (JP) .......................................... 10-150440

(51) Int. Cl.[7] .......................... A61M 37/00; A61B 17/08; A61B 17/32; B01D 61/00
(52) U.S. Cl. ....................... 604/5.04; 210/232; 210/645; 606/157; 606/167
(58) Field of Search .................... 604/35, 4.01, 60.6, 604/27, 34, 43, 93.01, 288.01, 288.02, 167, 120, 157, 29, 30

(56) References Cited

U.S. PATENT DOCUMENTS

| 4,716,886 A | * | 1/1988 | Schulman et al. | .......... | 128/305 |
| 4,856,517 A | * | 8/1989 | Collins et al. | .............. | 128/346 |
| 4,870,965 A | * | 10/1989 | Jahanger et al. | ............ | 128/318 |
| 5,520,699 A | * | 5/1996 | Hessel et al. | ................ | 606/120 |
| 5,556,404 A | * | 9/1996 | Belanger et al. | ............ | 606/151 |
| 5,584,840 A | * | 12/1996 | Ramsey et al. | .............. | 606/120 |
| 5,676,672 A | * | 10/1997 | Watson et al. | ............... | 606/120 |
| 5,817,116 A | * | 10/1998 | Takahashi et al. | ........... | 606/167 |
| 6,228,097 B1 | * | 5/2001 | Levinson et al. | ........... | 606/142 |

* cited by examiner

*Primary Examiner*—Angela D. Sykes
*Assistant Examiner*—Leslie R. Deak
(74) *Attorney, Agent, or Firm*—Wenderoth, Lind & Ponack, L.L.P.

(57) ABSTRACT

Disclosed is a new blood circuit detaching apparatus capable of detaching blood circuits under dialysis treatment from a dialyzer swiftly and safely during an emergency such as a fire or earthquake. The apparatus (2) for detaching dialyzing artery and vein plastic tubes blood circuits (1A) and (1B) from a dialyzer during an emergency, includes dialyzer side clamping portions (2A) and patient side clamping portions (2B) for clamping mounted blood circuits (1A) and (1B), circuit cutting portions (2C) arranged between the two clamping portions (2A) and (2B), and a pivotally moving cam mechanism for operating the dialyzer side clamping portions (2A), the patient side clamping portions (2B) and the circuit cutting portions (2C). By operating the pivotally moving cam mechanism, cutting at the circuit cutting portions (2C) is carried out successively with respect to clamping at the dialyzer side clamping portion (2A) and clamping at the patient side clamping portion (2B), to thereby detach the blood circuits (1A) and (1B) from the dialyzer.

22 Claims, 17 Drawing Sheets

Fig. 8
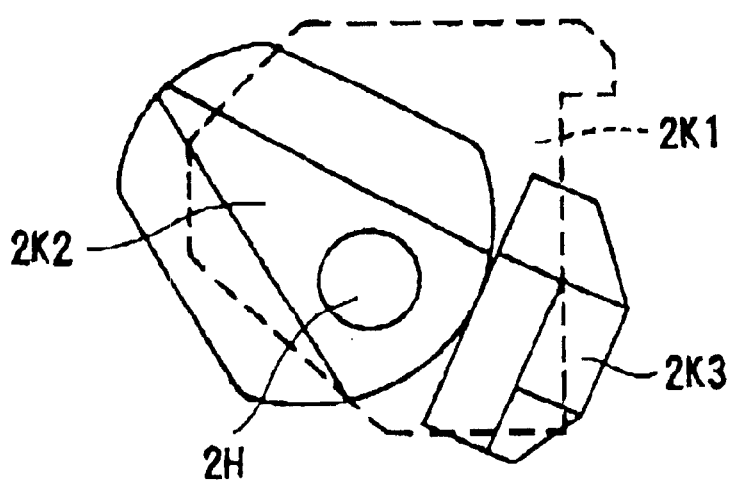
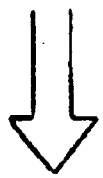
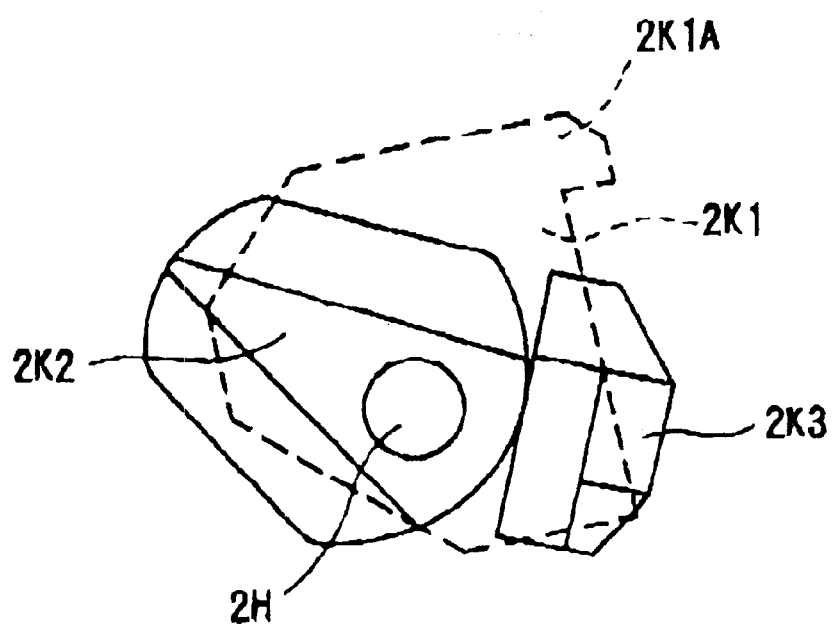

Fig. 10A
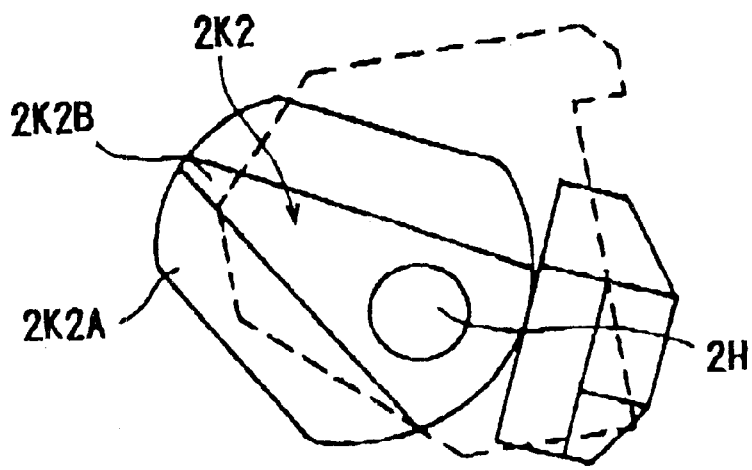
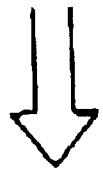
Fig. 10B
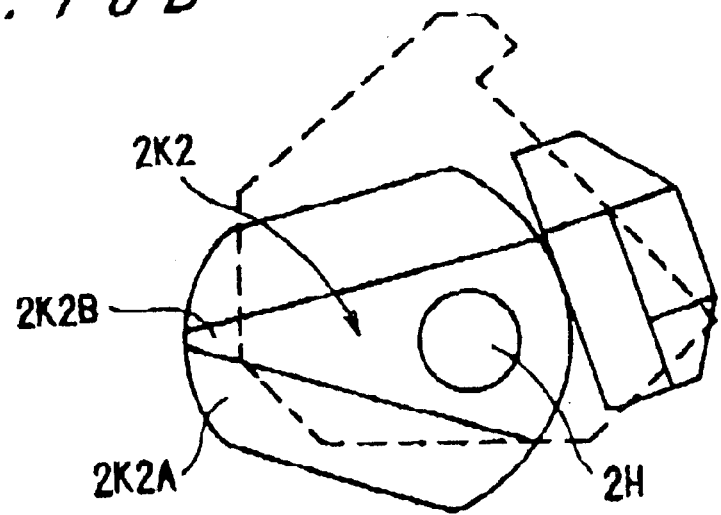

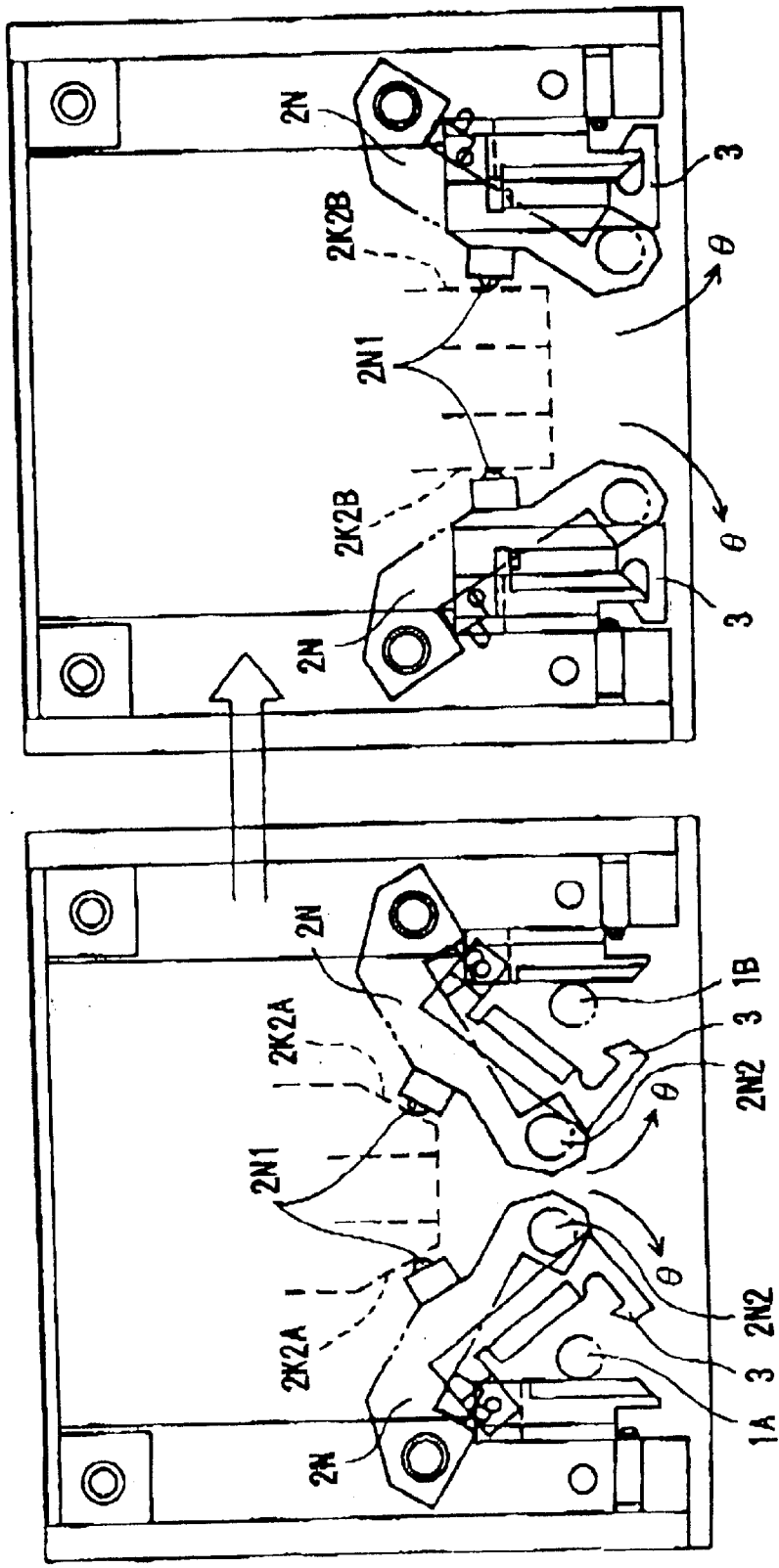

Fig. 15A
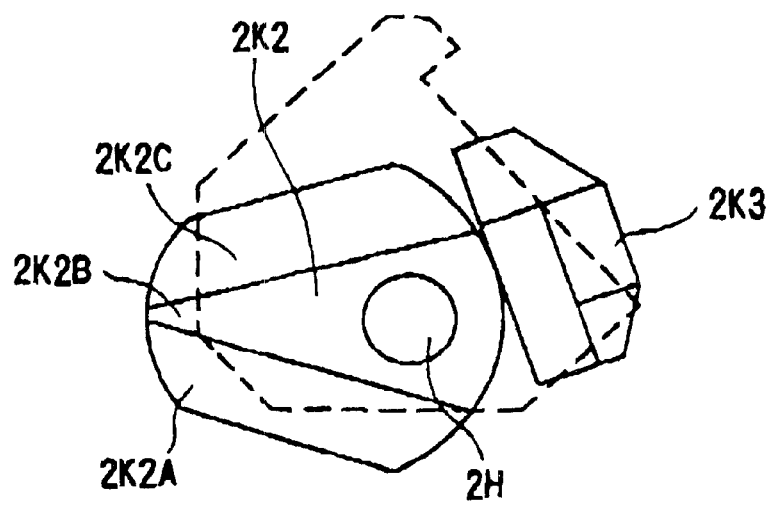
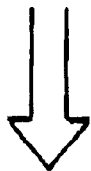
Fig. 15B
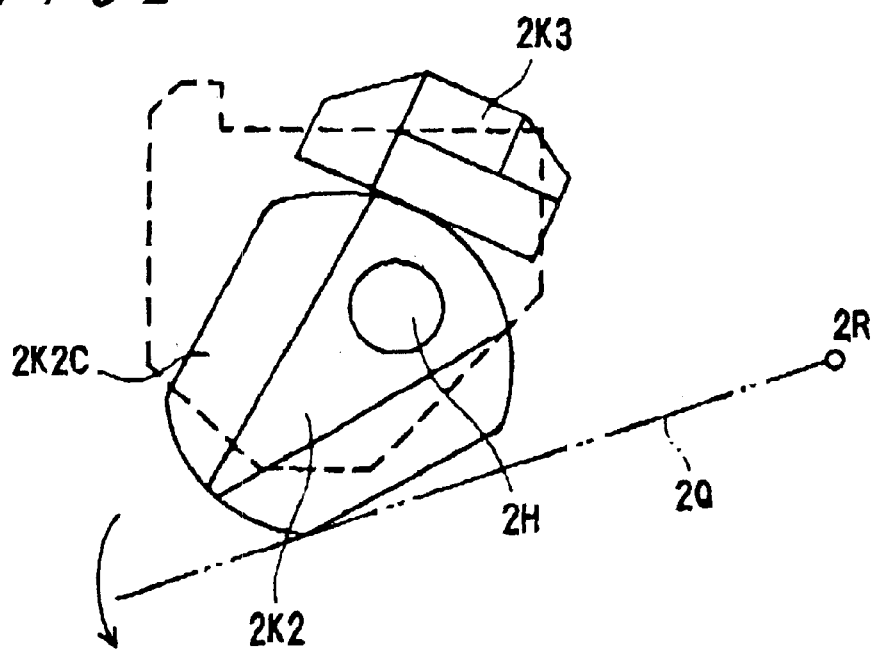

Fig. 16
PRIOR ART
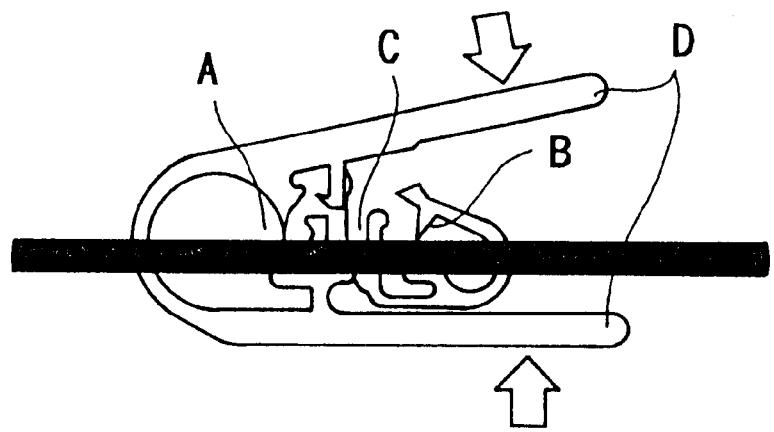
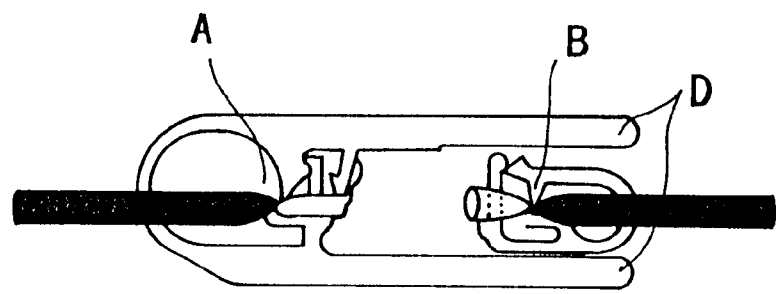

BLOOD CIRCUIT DETACHING APPARATUS

BACKGROUND OF THE INVENTION

1. Field of the Invention

The present invention relates to a blood circuit detaching apparatus. More particularly, the invention relates to a new and improved blood circuit detaching apparatus that is capable of detaching blood circuits from a dialyzer swiftly and safely in the midst of a dialyzing operation during an emergency such as a fire or earthquake.

2. Prior Art

A patient under dialysis is constrained to a dialyzer by blood circuits comprising artery and vein plastic tubes for dialysis, and accordingly, there has conventionally been recognized a necessity of swiftly detaching the blood circuits from the dialyzer during an emergency situation such as the occurrence of a fire or earthquake.

Further, with respect to the detaching operation, there must be ensured safety and the capability of carrying out a swift operation while causing no hindrance of the dialyzing operation, and that during an emergency situation the detachment is operable by a patient who is under dialysis.

In order to meet the request as much as possible, conventionally, there has widely been adopted means for clamping (squeezing to close) respective artery and vein blood circuits on the side of a dialyzer and on the side of a patient by using pairs of Pean forceps and then cutting intermediate portions of the blood circuits between the clamping positions on the side of the dialyzer and the clamping positions on the side of the patient by scissors to thereby detach the blood circuits from the dialyzer.

The detaching means comprising a combination of Pean forceps and scissors is put into a bag and is kept ready at bed side as an emergency kit.

However, in the case of the conventional detaching means comprising Pean forceps and scissors, since one hand of the patient under dialysis is connected to the blood circuits, the detaching means is operable only by the other hand. An operation of removing the Pean forceps and scissors from the bag, clamping the blood circuits by the Pean forceps and cutting them by the scissors, is very troublesome for the patient. Swift operation during an emergency while the patient is under an upset mental state is extremely difficult. Firm clamping may not be attained and cutting the blood circuits by using the scissors may even be dangerous.

In order to resolve such a problem as detaching means enabling swift one-hand operation, as shown by, for example, FIG. 16, there has been proposed and put into practical use an emergency detacher capable of clamping (A) on the side of a dialyzer, clamping (B) on the side of a patient, and circuit cutting (C), substantially simultaneously. As shown by FIG. 17, the emergency detacher is previously mounted to respective artery and vein blood circuits, and during an emergency respective pinching pieces (D) of the emergency detacher are squeezed by one hand to thereby clamp and cut the circuits.

In the case of the emergency detacher, there is certainly provided a feature in which the emergency detacher can be operated more conveniently than the combination of Pean forceps and scissors.

However, on the other hand, the detacher is of a shape and a size such that it is operable only by fingertips of one hand to simultaneously carry out the clamping and cutting operations. Therefore, about 7 kg of load is needed to perform the clamping and cutting operations by squeezing the pinching pieces (D), and there is a case in which the application of this load is difficult depending on the age, gender or physical condition of the patient. Further, according to the detacher, the squeezing operation must be carried out instantaneously since the operation involves simultaneous clamping and cutting. When the operation is interrupted midway therethrough, blood leaks out from partially cut blood circuits, which may be dangerous to the patient or a clean feeling may be lost due to the leakage of blood.

As has been described above, it is an actual situation of the conventional technology that there still is not realized means for emergency detachment in which swift and convenient operations are feasible, safety is ensured, a clean feeling is not deteriorated and one hand operation by a patient is facilitated.

SUMMARY OF THE INVENTION

It is an object of the invention to provide a new blood circuit detaching apparatus capable of resolving the above-described problems.

Hence, according to a first aspect of the invention, there is provided a blood circuit detaching apparatus which is an apparatus for detaching dialyzing artery and vein plastic tube blood circuits from a dialyzer during an emergency. The blood circuit detaching apparatus comprises a dialyzer side clamping portion and a patient side clamping portion, both for clamping mounted blood circuits. The apparatus also comprises a circuit cutting portion arranged between the two clamping portions, and a pivotally moving cam mechanism for operating the dialyzer side clamping portion, the patient side clamping portion and the circuit cutting portion. Through operation of the cam mechanism, the blood circuits are detached from the dialyzer by carrying out a cutting operation at a circuit cutting portion after a clamping operation at the dialyzer side clamping portion and a clamping operation at the patient side clamping portion are performed.

Further, according to a second aspect of the invention, there is provided the blood circuit detaching apparatus according to the first aspect, wherein the pivotally moving cam mechanism comprises a lever handle, a shaft to be pivoted by operating the lever handle, and cams fixed to the shaft. According to a third aspect of the invention, there is provided the blood circuit detaching apparatus according to the first or the second aspect, wherein the patient side clamping portion is provided with forceps members and the forceps members are attached to the blood circuits in a clamped state during the clamping operation. According to a fourth aspect of the invention, there is provided the blood circuit detaching apparatus according to any one of the first through the third aspects, further comprising a fixedly attaching portion for attaching the apparatus to a supporter. Further, according to a fifth aspect of the invention, there is provided the blood circuit detaching apparatus according to any one of the first through the fourth aspects, wherein the dialyzer side clamping portion, the circuit cutting portion and the patient side clamping portion are arranged in this order in an up to down direction.

BRIEF DESCRIPTION OF THE DRAWINGS

FIG. 8 is a side view showing motion of the cams up to the clamping operation on the side of a dialyzer;

FIGS. 10A and 10B are side views showing motion of the cams up to a clamping operation on the side of a patient;

FIGS. 11A and 11B are plane views of essential portions showing a clamping operation in correspondence with FIGS. 10A and 10B;

FIGS. 15A and 15B are side views of essential portions showing motion of the cams in correspondence with FIG. 13 and FIG. 14;

FIG. 16 is a view of essential portions exemplifying a conventional emergency detacher.

DETAILED DESCRIPTION OF THE INVENTION

A detailed explanation will be given of an embodiment of a blood circuit detaching apparatus according to the invention having the above-described features in reference to the attached drawings.

Figure 1:
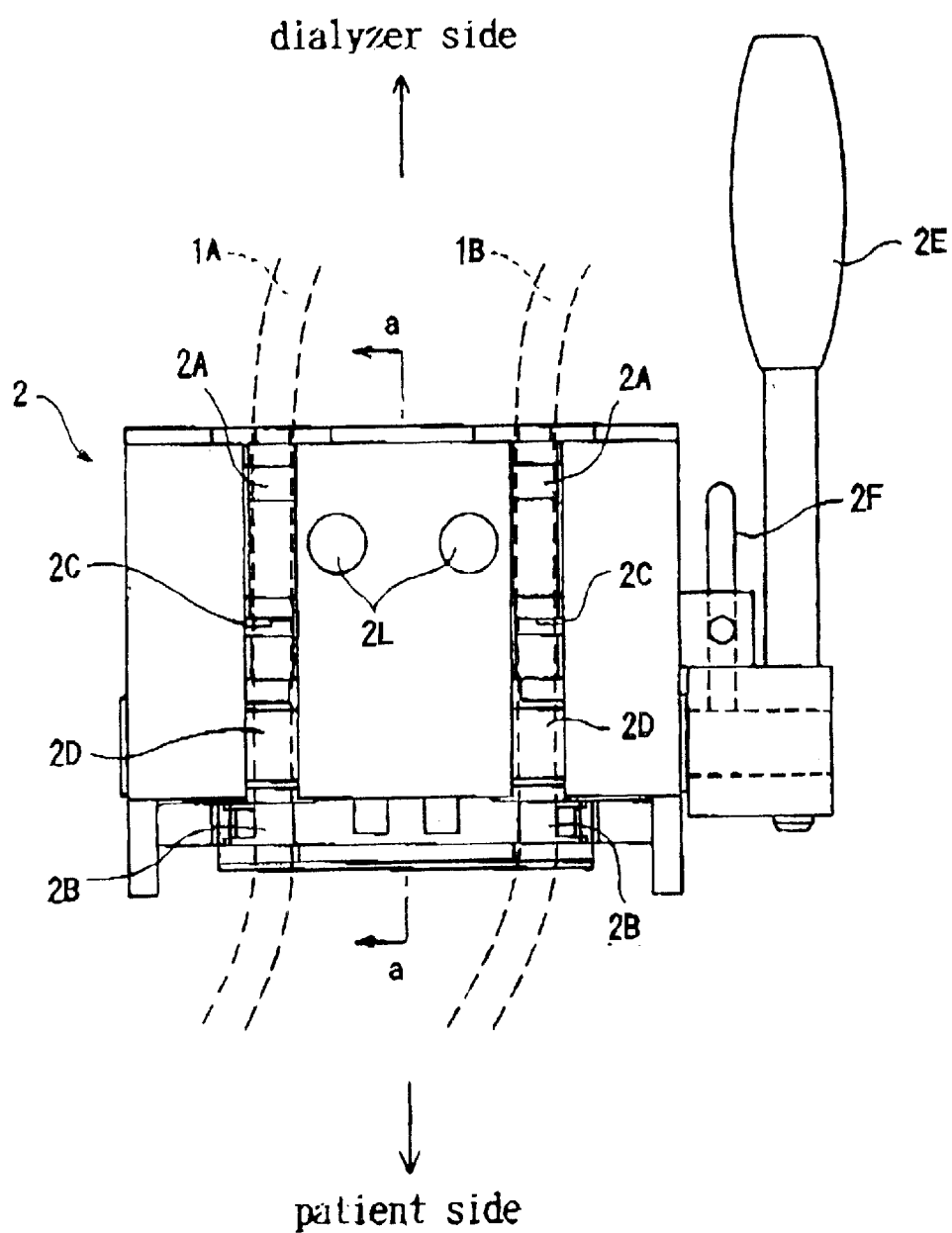
FIG. 1 is a front view of an apparatus according to an embodiment of the invention.
Figure 2:
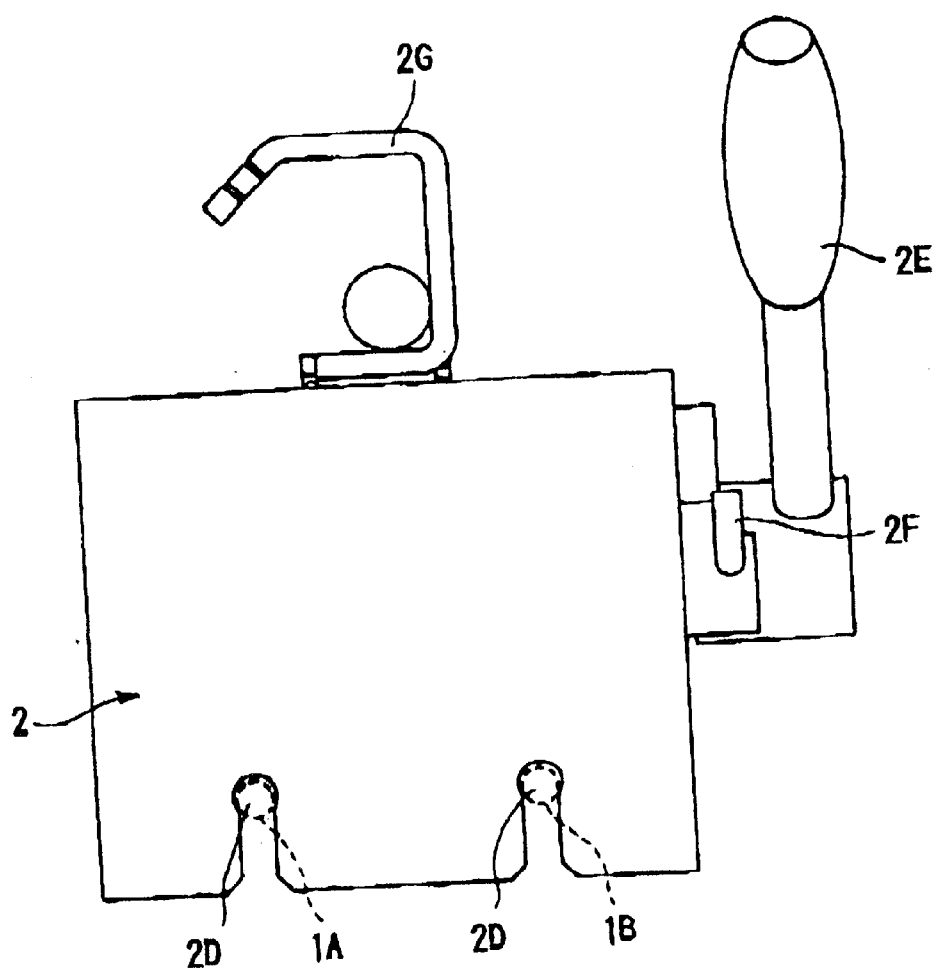
FIG. 2 is a plane view in correspondence with FIG. 1.
Figure 3:
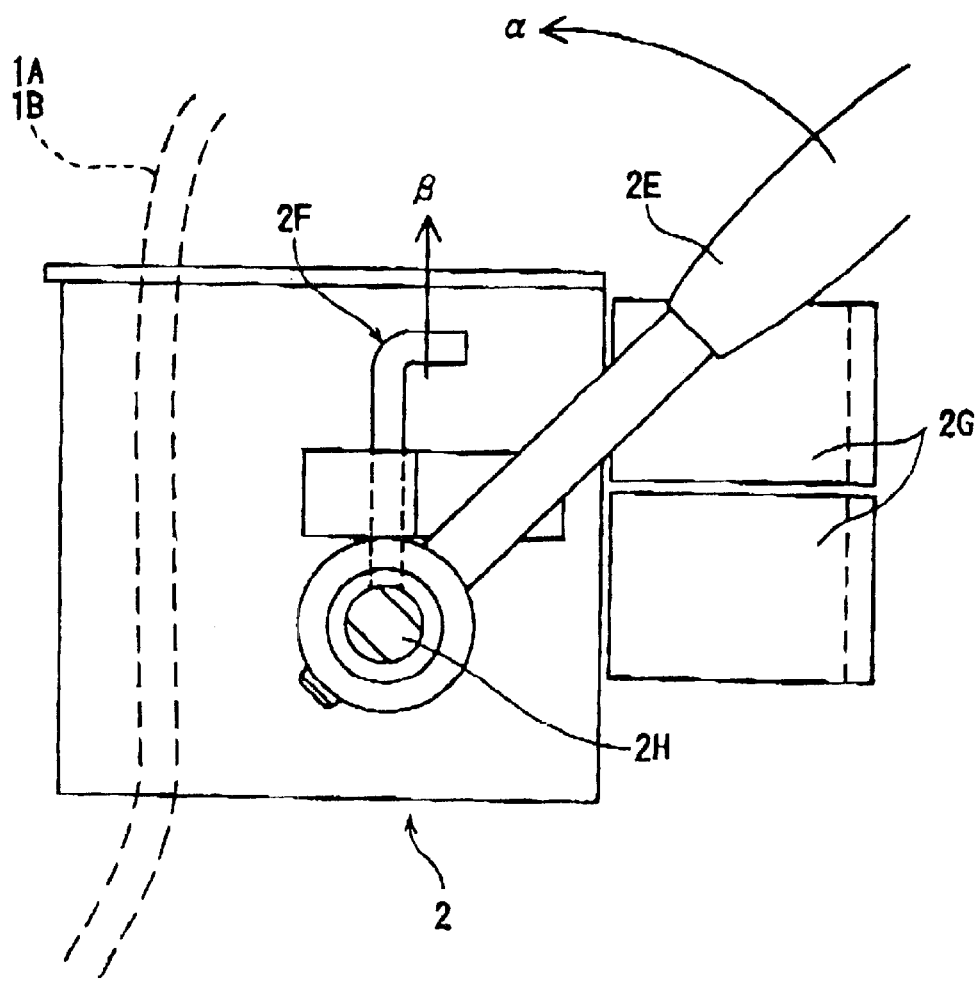
FIG. 3 is a side view in correspondence with FIG. 1.

FIG. 1, FIG. 2 and FIG. 3 are a front view, a plane view and a side view showing an example of a blood circuit detaching apparatus according to the invention. As exemplified in these drawings, an apparatus (2) for detaching dialyzing artery and vein plastic tube blood circuits (1A) and (1B) from a dialyzer during an emergency, includes dialyzer side clamping portions (2A) and patient side clamping portions (2B) for clamping artery and vein blood circuits (1A) and (1B) mounted in groove portions (2D) installed in the up and down direction on the front side, and also includes circuit cutting portions (2C) arranged between the two clamping portions (2A) and (2B).

Further, according to the example of the detaching apparatus (2), there is provided a lever handle (2E) to facilitate one hand operation even by a patient per se. The blood circuits (1A) and (1B) can be detached from a dialyzer by pivoting the lever handle (2E) from an original point portion in normal time shown by, for example, FIG. 3 in a direction of an arrow mark a in the drawing.

In normal time, a stopper pin (2F) is locked to the lever handle (2E) and accordingly, the lever handle (2E) cannot be pivoted. During an emergency, pivotal operation of the lever handle (2E) can be carried out by drawing the stopper pin (2F) upwardly, that is, in a direction of an arrow mark β of FIG. 3.

Further, the detaching apparatus (2) according to the example is provided with a fixedly attaching portion (2G) to be able to be stably fixed to a supporter of a bed side console or the like. The fixedly attaching portion (2G) as well as a mechanism for pivoting and locking the lever handle (2E) and the stopper pin (2F), may be formed in various shapes and structures.

Further, needless to explain, according to the above-described example, as shown by FIG. 1, upper sides of the blood circuits (1A) and (1B) are connected to a dialyzer and lower sides thereof are connected to a patient.

Further, according to the detaching apparatus (2) of the example, a shaft (2H) is pivoted by pivoting the lever handle (2E) and at the same time, cams fixed to the shaft (2H) are rotated. That is, the detaching apparatus (2) is installed with a pivotally moving cam mechanism for operating the dialyzer side clamping portions (2A), the patient side clamping portions (2B) and the circuit cutting portions (2C).

It is a significant feature of the invention that the blood circuits (1A) and (1B) are detached from a dialyzer by carrying out a clamping operation at the dialyzer side clamping portions (2A), the clamping operation at the patient side clamping portions (2B) and then a cutting operation of the circuit cutting portions (2C) by the pivotally moving cam mechanism.

Figure 4:
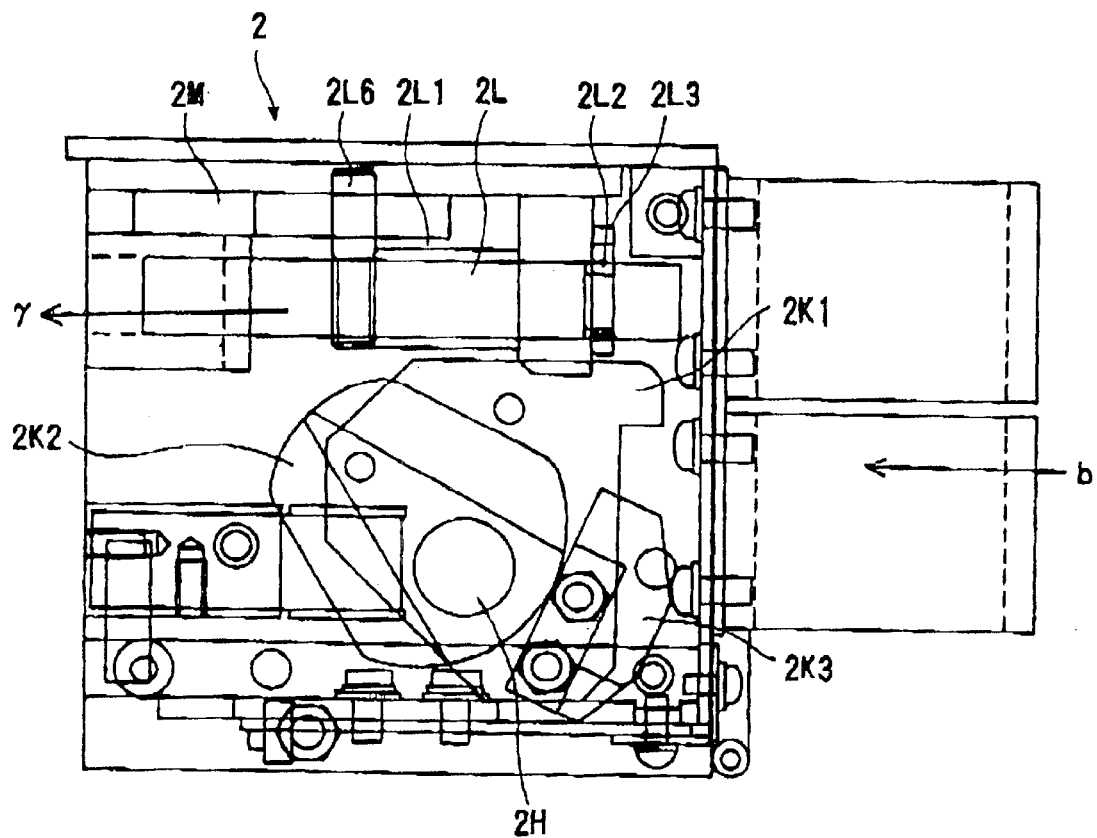
FIG. 4 is a sectional view viewing the apparatus in a direction of arrow marks a—a of FIG. 1.

FIG. 4 shows a sectional view viewing FIG. 1 in a direction of arrow marks a—a. The cams constituting the cam mechanism comprise three kinds of cams (2K1), (2K2) and (2K3).

Figure 5:
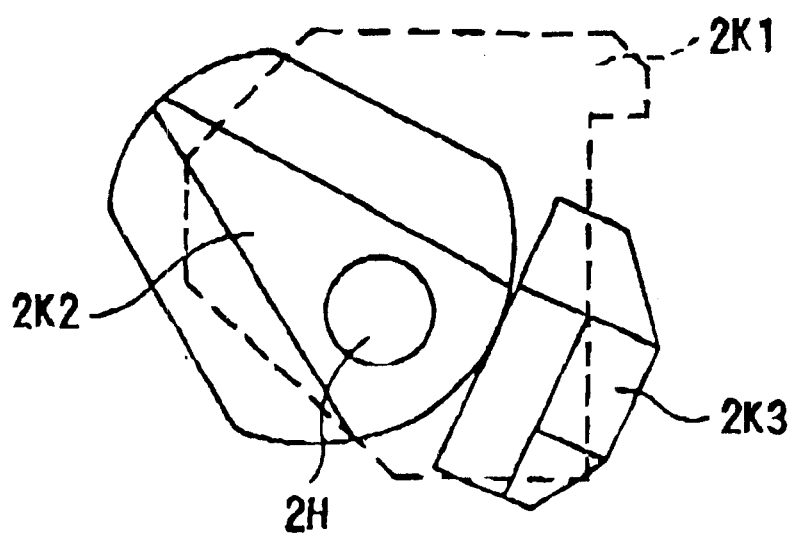
FIG. 5 is a side view exemplifying a constitution of cams.

A position at which the lever-handle (2E) is stopped, such that the lever handle (2E) cannot be pivoted by locking it by the stopper pin (2F), is referred to as "original point position". FIG. 4 is a sectional view at the original point position and FIG. 5 shows only the three kinds of cams (2K1), (2K2) and (2K3) and the shaft (2H) at the original point position. The cams (2K1), (2K2) and (2K3) may be fixedly attached to the shaft (2H) by fabricating them as respectively separate members or may be fabricated as an integrally formed article. As a relationship among these cams, according to the example, the cam (2K1) corresponds to the operation of clamping the blood circuits (1A) and (1B) at the dialyzer side clamping portions (2A), the cam (2K2) corresponds to the operation of clamping the blood circuits (1A) and (1B) at the patient side clamping portions (2B), and the cam (2K3) corresponds to the operation of cutting the blood circuits (1A) and (1B) at the cutting portions (2C). When these cams are constituted as respectively separate members, for example, the cams (2K2) and the cams (2K3) are arranged at both sides of the cam (2K1) as plate-like shapes.

Now, an explanation will be given to exemplify operation of the cams (2K1), (2K2) and (2K3) as follows.

(1) Clamping Operation at the Dialyzer Apparatus Side Clamping Portion (2A)

Figure 6:
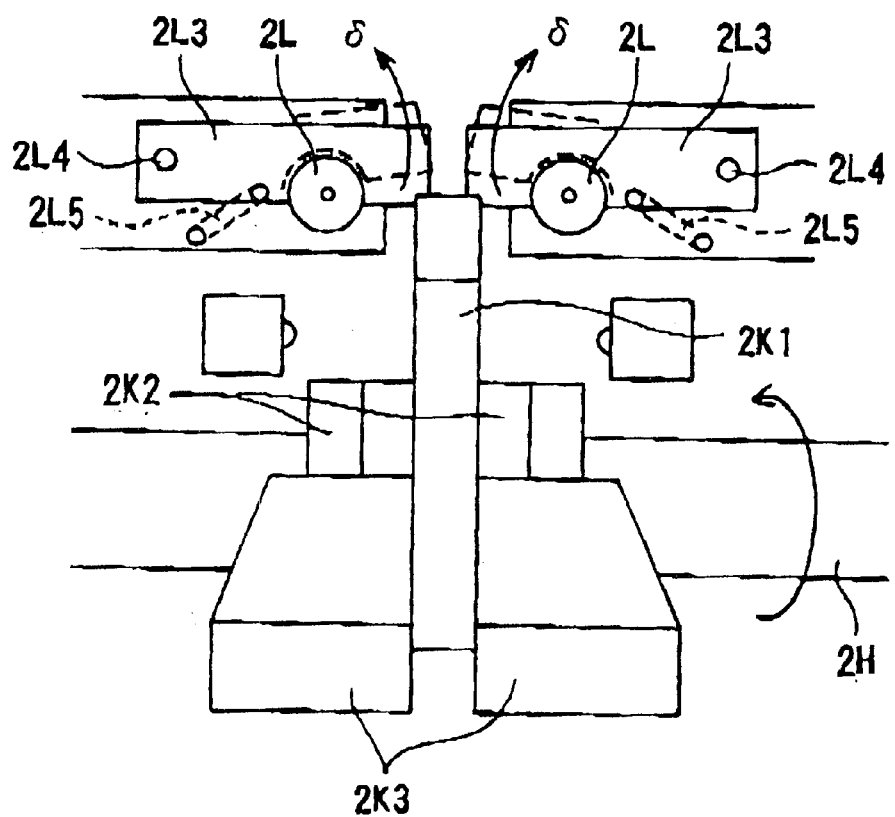
FIG. 6 is a rear view of essential portions in correspondence with FIG. 1.

As mentioned above, FIG. 4 is the sectional view viewing FIG. 1 in the direction of the arrow marks a—a, and FIG. 6 is a rear view of essential portions of the detaching apparatus (2) according to the example, that is, a view viewing FIG. 4 in a direction of an arrow mark "b".

As is seen in FIG. 4 and FIG. 6 showing the arrangement at the original point position, the detaching apparatus (2) is provided with slide bars (2L) at its upper portion and the slide bars (2L) are urged in a direction of an arrow mark γ in FIG. 4 by springs (2L1). Further, the slide bars (2L) are provided with small diameter portions (2L2). The small diameter portions (2L2) are engaged with stopper pieces (2L3) also shown by FIG. 6. At the original point position, sliding movement of the slide bars (2L) in the direction γ are stopped despite urging of the springs (2L1) in the direction γ.

As shown also by FIG. 6, the stopper pieces (2L3) are pulled downwardly by springs (2L5) centering on fulcra (2L4). By the pulling force, the stopper pieces (2L3) are brought into a state in which they are fitted into engagement with the small diameter portions (2L2) of the slide bars (2L). Therefore, the stopper pieces (2L3) are not moved even when they are urged in the direction γ by the springs (2L1).

The slide bars (2L) serve a role for performing the clamping operation at the dialyzer side clamping portions (2A), and the role in this case is achieved by moving the slide bars (2L) in the direction γ by being urged by the springs (2L1).

That is, engaging pins (2L6) are erected on the slide bars (2L). As exemplified in FIG. 7, the movement of the engaging pins (2L6) rotate clamp pieces (2M) to thereby firmly clamp the blood circuits (1A) and (1B) in the groove portions (2D). The press force of the engaging pins (2L6) exerted on the clamp pieces (2M) becomes large as an urge force of the springs (2L1) is exerted on the slide bars (2L), by which the clamping operation at the dialyzer apparatus side clamping portions (2A) is firmly carried out.

It is a condition of such a clamping operation to move the slide bars (2L) in the direction γ. The movement is realized by the cam (2K1) mentioned above.

Figure 7:
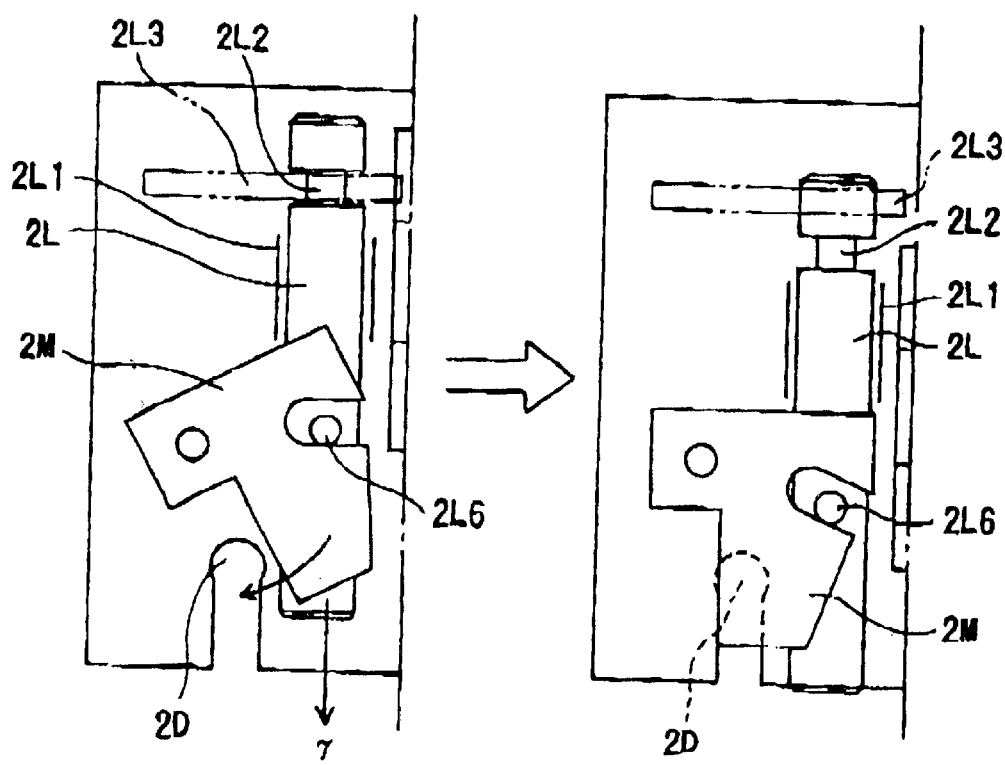
FIG. 7 is a plane view of essential portions exemplifying a clamping operation at a dialyzer side clamping portion.

That is, as shown also by FIG. 7, the movement of the slide bars (2L) is realized by disengaging the stopper pieces (2L3) from the small diameter portions (2L2) of the slide bars (2L). As shown by FIG. 6, the stopper pieces (2L3) urged downwardly are pushed up in the upward direction of the drawing by pivoting the cam (2K1) in accordance with the pivotal movement of the shaft (2H) in the direction of an arrow mark by operating the lever handle (2E), to thereby rotate in directions d by which fitted attachment of the stopper pieces (2L3) to the small diameter portions (2L2) is released and movement of the slide bars (2L) in the direction γ is started.

Figure 9:
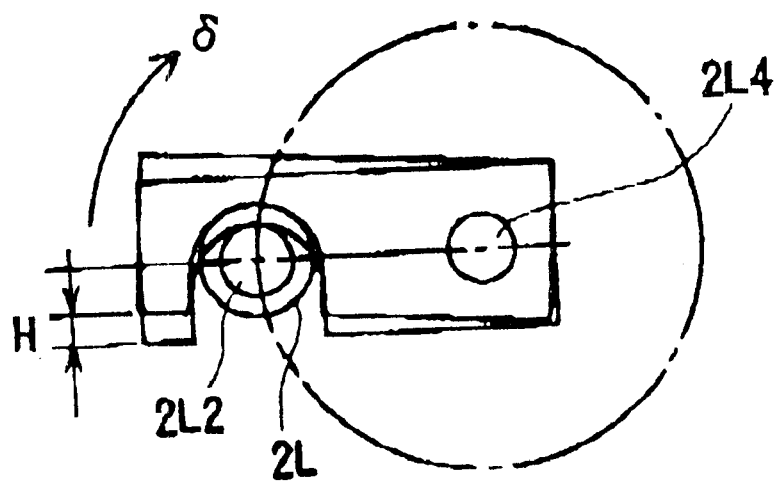
FIG. 9 is a rear view of essential portions showing motion of a stopper piece.

FIG. 8 shows motion of the cam (2K1) during this occasion. For example, a corner portion (2K1A) of the cam (2K1) pushes up the stopper pieces (2L3), and fitted attachment of the stopper pieces (2L3) to the small diameter portions (2L2) is released. FIG. 9 shows a height of variation (H) when the stopper piece (2L3) is pushed up.

(2) Clamping Operation at the Patient Side Clamping Pportion (2B)

When the lever handle (2E) is further turned, the shaft (2H) is pivoted and the cams are also pivoted in accordance therewith. By the pivotal movement, the clamping of the blood circuits (1A) and (1B) is successively carried out at the patient side clamping portion (2B).

In this case, the clamping operations are performed by operating the cams (2K2), as mentioned above.

Figure 12A:
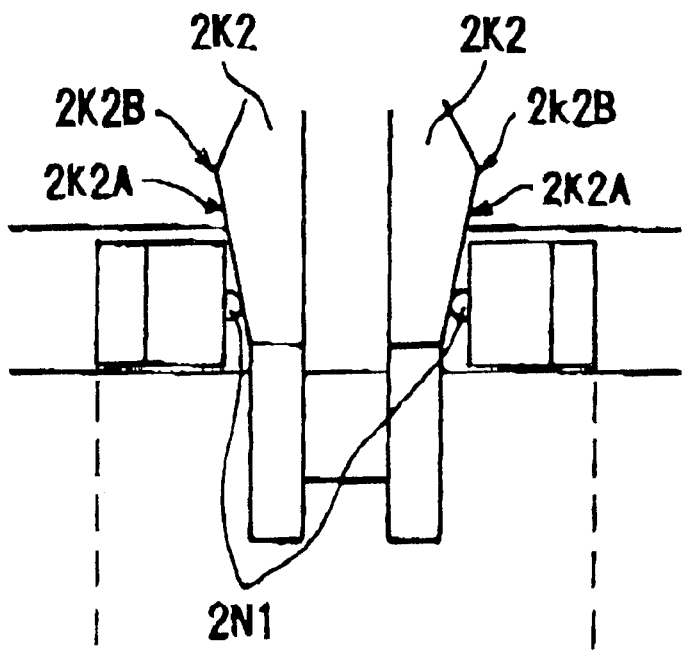
FIGS. 12A and 12B are front views of essential portions showing motion of the cams in correspondence with FIGS. 10A and 10B and FIGS. 11A and 11B.
Figure 12B:
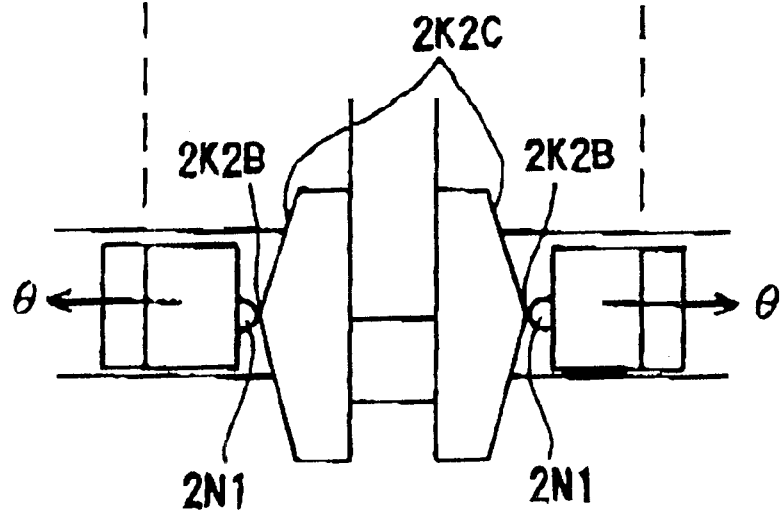

FIGS. 10A and 10B show a change in the pivotal state of the cam (2K2) for enabling the clamping operation at the patient side clamping portion (2B), and FIGS. 10A and 10B also show a change further from the state of FIG. 8. Further, FIGS. 11A and 11B and FIGS. 12A and 12B show motion of clamp pieces (2N) and projections (2N1) thereof in accordance with the pivotal movement of the cams (2K2). FIG. 10A, FIG. 11A and FIG. 12A show a state before clamping. In this example, the projections (2N1) of the clamp pieces (2N) are moved while being in contact with inclined faces (2K2A) on the lower sides of the cams (2K2) toward peak portions (2K2B) thereof. In accordance therewith, the clamp pieces (2N) are rotated in a direction θ and the pins (2N2) push forceps (3), to be attached to the blood circuits on the patient side in the clamped state, to the sides of the blood circuits (1A) and (1B).

When the projections (2N1) reach the peak portions (2K2B) of the cams (2K2), that is, in the state of FIG. 10B and FIG. 11B, the operation of clamping the blood circuits (1A) and (1B) by the forceps (3) by using the clamp pieces (2N) is completed.

Although in the clamping operation on the patient side, it is preferable to use the forceps (3) attached firmly to the circuits in the clamped state in consideration of movement of the patient after the detachment by walking or the like, separate holding means for creating the clamped state may be considered.

In any event, according to the detaching apparatus (2), the clamp pieces (2N) are rotated in the direction θ by being pushed by strong forces by using the cams (2K2), and accordingly, a firm clamping operation can be executed.

(3) Cutting Operation of the Blood Circuits

The blood circuits (1A) and (1B) are cut by further pivoting the lever handle (2E). The cutting is made feasible by pivoting the cams (2K3).

Figure 13:
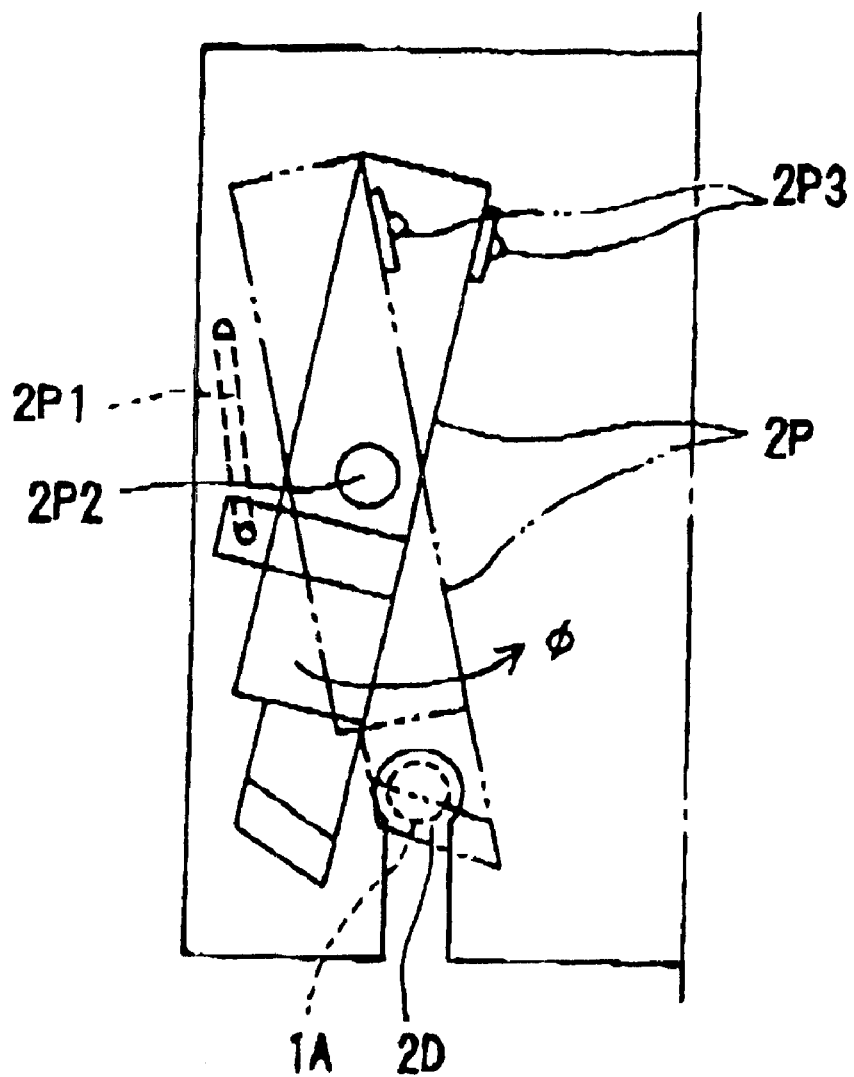
FIG. 13 is a plane view of essential portions exemplifying motion of a cutting edge at a cutting portion.

The cutting operation is carried out by pivoting cutting edges (2P) exemplified in, for example, FIG. 13 at the cutting portions (2C) shown in FIG. 1. That is, by pivoting the cutting edges (2P) about fulcra (2P2), which cutting edges (2P) are pulled by springs (2P1), the blood circuits (1A) and (1B) in the grooves (2D) are cut.

According to the example of FIG. 13, the pivotal movement is caused by moving projections (2P3), as contact portions of the cutting edges (2P), in response to being pushed by the cams (2K3). The motion of the cams (2K3) may be regarded as a change from the original point positions of FIG. 6 to positions in the state as shown in a rear view of FIG. 14, and further, as a change as shown in FIGS. 15A and 15B.

Figure 14:
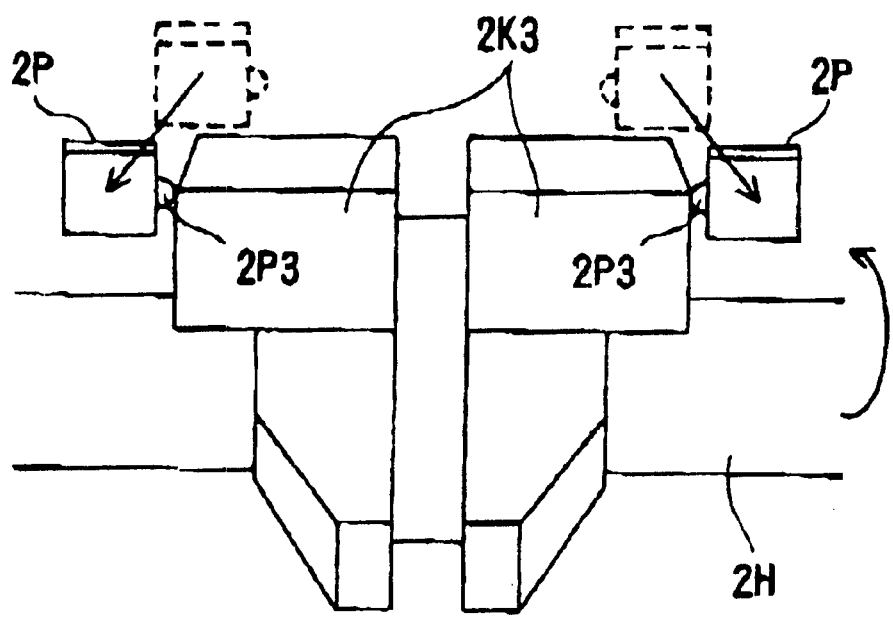
FIG. 14 is a rear view of essential portions showing motion of the cams in correspondence with FIG. 13.

The cutting edges (2P) are pivotally moved in the direction φ by movement of the projections (2P3) following the inclined faces of the cams (2K3), that is, by relative movement as shown by an arrow mark in FIG. 14.

By the cutting operation mentioned above, the blood circuits (1A) and (1B) are detached from the dialyzer.

(4) Detaching Operation After Cutting the Patient Side Circuits

Further, additional explanation is given with regard to the detaching apparatus (2) exemplified above. When the cutting operation is completed, the blood circuits in the clamped state on the side of the patient can immediately be relieved of the detaching apparatus (2).

As shown by FIGS. 12A and 12B and FIGS. 15A and 15B, the cams (2K2) for executing the clamping operation on the side of the patient, are provided with inclined faces (2K2C) on upper sides thereof. The projections (2N1) of the clamp pieces (2N) are moved to follow the upper side inclined faces (2K2C) from the peak portions (2K2B). Therefore, a press force for performing the clamping operation by the clamp pieces (2N) is released at a stroke, and the patient side circuits which have been clamped by the forceps (3) are immediately detached from the apparatus (2) after the cutting operation.

During this occasion, when the apparatus (2) is installed with a bottom plate (2Q) which can be pivoted around a fulcrum (2R), the cams (2K2) may be brought into contact with the bottom plate (2Q) to thereby push the bottom plate (2Q) to an open position as shown by FIG. 15B. In this way, even when the bottom plate (2Q) is provided on the apparatus (2), the patient side circuits can be detached smoothly after cutting.

(5) Returning Operation to the Original Point Position

It is easy to again set the detaching apparatus (2) after the emergency state has been resolved.

The lever handle (2E) is reversely rotated to return to the state shown by FIGS. 1 through 3. Further, front ends of the slide bars (2L) shown in FIG. 1 are pushed in by the stopper pin (2F) to thereby return to a state in which the small diameter portions (2L2) are fitted with the stopper pieces (2L3).

As has been explained in detail, the following operations are carried out successively and swiffly by only turning the lever handle (2E) owing to the cam mechanism.

(1) Clamping operation on the side of a dialyzer
(2) Clamping operation on the side of a patient
(3) Operation of cutting circuits It is conceivable to adopt electric means such as a motor in place of the lever handle (2E) and it is also conceivable to use the electric means as auxiliary means. In consideration that even by using the lever handle (2E), the patient per se can swiftly operate the apparatus by one hand with no need of applying a large force, with the lever handle (2E) the patient can interrupt the operation midway therethrough and stop the operation in the state where the blood circuits have been clamped during an earthquake since rocking is not caused, and the manual operation is preferable in view of the cost. The apparatus can be made sufficiently practical by providing the lever handle, or a structure functionally similar thereto in the detaching apparatus during an emergency.

When an electric system is adopted, the control poses a problem with regard to handling by a patient and a burden in view of the cost must be considered. However, the invention does not exclude the use of an electric system, and includes it as one mode of the invention.

Figure 17:
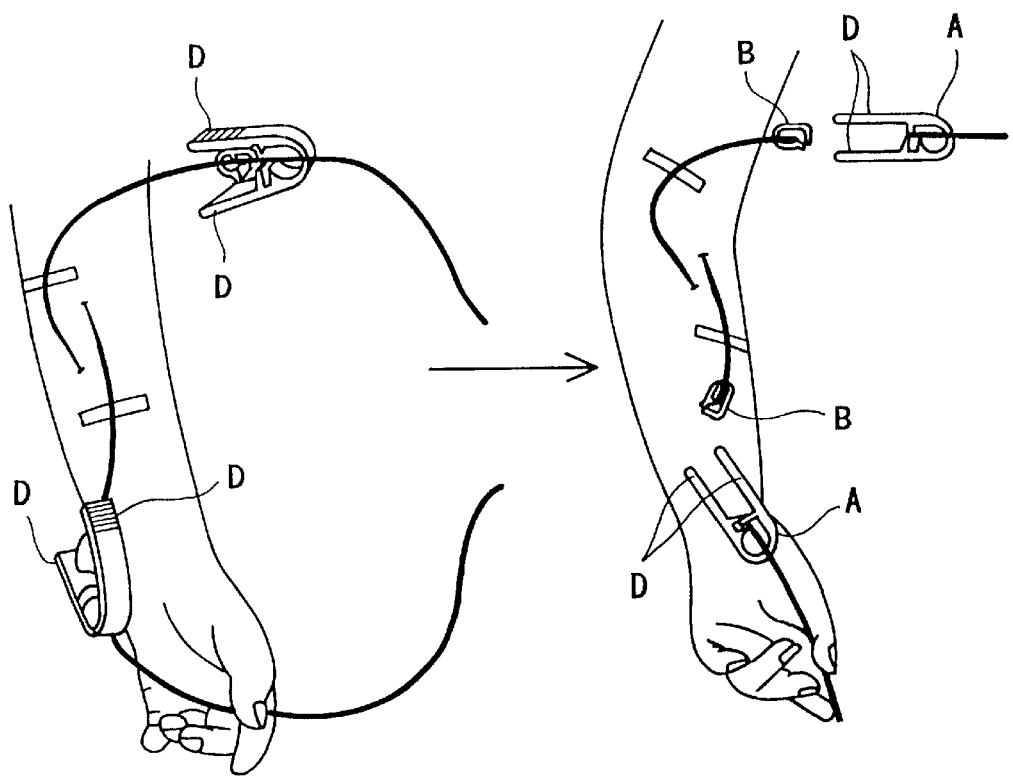
FIG. 17 is a view showing an example of using the emergency detacher of FIG. 16.

When the function of the detaching apparatus (2) exemplified in FIGS. 1 through 15B is evaluated in view of the operation of a patient, an average value of the operational time period is 4.9±1.5 seconds, which is significantly shorter than 52.35 18.1 seconds in the case of a set of Pean forceps and scissors. Further, in the case of the detacher exemplified in FIGS. 16 and 17, the average value is 7.2±2.5 seconds. It is found that the operation can be carried out swifter with the detaching apparatus (2) of the instant invention than with the detacher of FIGS. 16 and 17.

Further, in the case of the operation of the detaching apparatus (2) by the lever handle according to the example, all of patients can handle the apparatus by one hand, whereas in the case of the set of Pean forceps and scissors and in the case of the above-described conventional detacher, there are recognized patients who cannot handle the apparatus with one hand.

Furthermore, in the case of the detaching apparatus (2), safety is excellent and there is no inconvenience produced by leaking blood.

Naturally, the apparatus of the invention is not limited to the description with reference to the drawings. It goes without saying that various modes in implementing the apparatus are pertinently considered with respect to a constitution of the detailed portions, the shape, the size and the structure of the apparatus.

As has been explained in detail, there is provided by the instant invention a detaching apparatus that is excellent for swift detachment during a dialyzing operation, and provides a safe and clean feeling. According to the apparatus, one hand operation by a patient per se is facilitated and an emergency arising in the midst of medical treatment of blood dialysis at a facility or at home can be dealt with perfectly.

What is claimed is:

1. A blood circuit detaching apparatus for simultaneously detaching a dialyzing artery plastic tube blood circuit and a dialyzing vein plastic tube blood circuit from a dialyzer, comprising:

two groove portions for receiving therein the dialyzing artery plastic tube blood circuit and the dialyzing vein plastic tube blood circuit, respectively;

two dialyzer side clamping portions for clamping a dialyzer-side part of the dialyzing artery plastic tube blood circuit and a dialyzer-side part of the dialyzing vein plastic tube blood circuit, respectively, when the dialyzing artery plastic tube blood circuit and the dialyzing vein plastic tube blood circuit are respectively received within said two groove portions;

two patient side clamping portions for clamping a patient-side part of the dialyzing artery plastic tube blood circuit and a patient-side part of the dialyzing vein plastic tube blood circuit, respectively, when the dialyzing artery plastic tube blood circuit and the dialyzing vein plastic tube blood circuit are respectively received within said two groove portions;

two circuit cutting portions for cutting the dialyzing artery plastic tube blood circuit and the dialyzing vein plastic tube blood circuit, respectively, between the patient-side part and the dialyzerside part when the dialyzing artery plastic tube blood circuit and the dialyzing vein plastic tube blood circuit are respectively received within said two groove portions and clamped by said two dialyzer side clamping portions and said two patient side clamping portions, said two circuit cutting portions being arranged between said two dialyzer side clamping portions and said two patient side clamping portions, respectively; and a cam mechanism constructed and arranged to pivotally move such that said two dialyzer side clamping portions are activated to respectively clamp the dialyzer-side part of the dialyzing artery plastic tube blood circuit and the dialyzer-side part of the dialyzing vein plastic tube blood circuit and said two patient side clamping portions are activated to respectively clamp the patient-side part of the dialyzing artery plastic tube blood circuit and the patient-side part of the dialyzing vein plastic tube blood circuit, and then said two circuit cutting portions are activated to respectively cut the dialyzing artery plastic tube blood circuit and the dialyzing vein plastic tube blood circuit between the patient-side part and the dialyzer-side part, whereby the dialyzing artery plastic tube blood circuit and the dialyzing vein plastic tube blood circuit become simultaneously detached from the dialyzer.

2. The blood circuit detaching apparatus according to claim 1, wherein said cam mechanism includes a lever handle, a shaft to be pivoted by operating said lever handle, and cams fixed to said shaft.

3. The blood circuit detaching apparatus according to claim 2, wherein said two patient side clamping portions include forceps members that are to clamp the patient-side part of the dialyzing artery plastic tube blood circuit and the patient-side part of the dialyzing vein plastic tube blood circuit, respectively.

4. The blood circuit detaching apparatus according to claim 2, further comprising a portion to be attached to a support.

5. The blood circuit detaching apparatus according to claim 2, further comprising an upper side and a lower side, with said two dialyzer side clamping portions provided at said upper side, said two patient side clamping portions provided at said lower side, and said two cutting portions provided between said upper side and said lower side.

6. The blood circuit detaching apparatus according to claim 1, wherein said two patient side clamping portions include forceps members that are to clamp the patient-side part of the dialyzing artery plastic tube blood circuit and the patient-side part of the dialyzing vein plastic tube blood circuit, respectively.

7. The blood circuit detaching apparatus according to claim 6, further comprising a portion to be attached to a support.

8. The blood circuit detaching apparatus according to claim 6, further comprising an upper side and a lower side, with said two dialyzer side clamping portions provided at said upper side, said two patient side clamping portions provided at said lower side, and said two cutting portions provided between said upper side and said lower side.

9. The blood circuit detaching apparatus according to claim 1, further comprising a portion to be attached to a support.

10. The blood circuit detaching apparatus according to claim 9, further comprising an upper side and a lower side, with said two dialyzer side clamping portions provided at said upper side, said two patient side clamping portions provided at said lower side, and said two cutting portions provided between said upper side and said lower side.

11. The blood circuit detaching apparatus according to claim 1, further comprising an upper side and a lower side, with said two dialyzer side clamping portions provided at said upper side, said two patient side clamping portions provided at said lower side, and said two cutting portions provided between said upper side and said lower side.

12. A blood circuit detaching apparatus for detaching a dialyzing artery plastic tube blood circuit and a dialyzing vein plastic tube blood circuit from a dialyzer, comprising:

two groove portions for receiving therein the dialyzing artery plastic tube blood circuit and the dialyzing vein plastic tube blood circuit, respectively;

a dialyzer side clamping mechanism for clamping a dialyzer-side part of the dialyzing artery plastic tube blood circuit and a dialyzer-side part of the dialyzing vein plastic tube blood circuit when the dialyzing artery plastic tube blood circuit and the dialyzing vein plastic tube blood circuit are respectively received within said two groove portions;

a patient side clamping mechanism for clamping a patient-side part of the dialyzing artery plastic tube blood circuit and a patient-side part of the dialyzing vein plastic tube blood circuit when the dialyzing artery plastic tube blood circuit and the dialyzing vein plastic tube blood circuit are respectively received within said two groove portions;

a circuit cutting mechanism for cutting the dialyzing artery plastic tube blood circuit and the dialyzing vein plastic tube blood circuit between the patient-side part and the dialyzer-side part when the dialyzing artery plastic tube blood circuit and the dialyzing vein plastic tube blood circuit are respectively received within said two groove portions and clamped by said dialyzer side clamping mechanism and said patient side clamping mechanism, said circuit cutting mechanism being arranged between said dialyzer side clamping mechanism and said patient side clamping mechanism; and a cam mechanism constructed and arranged to pivotally move such that said dialyzer side clamping mechanism is activated to clamp the dialyzer-side part of the dialyzing artery plastic tube blood circuit and the dialyzer-side part of the dialyzing vein plastic tube blood circuit and said patient side clamping mechanism is activated to clamp the patient-side part of the dialyzing artery plastic tube blood circuit and the patient-side part of the dialyzing vein plastic tube blood circuit, and then said circuit cutting mechanism is activated to cut the dialyzing artery plastic tube blood circuit and the dialyzing vein plastic tube blood circuit between the patient-side part and the dialyzer-side part, whereby the dialyzing artery plastic tube blood circuit and the dialyzing vein plastic tube blood circuit become detached from the dialyzer.

13. The blood circuit detaching apparatus according to claim 12, wherein said cam mechanism includes a lever handle, a shaft to be pivoted by operating said lever handle, and cams fixed to said shaft.

14. The blood circuit detaching apparatus according to claim 13, wherein said patient side clamping mechanism includes forceps members that are to clamp the patient-side part of the dialyzing artery plastic tube blood circuit and the patient-side part of the dialyzing vein plastic tube blood circuit.

15. The blood circuit detaching apparatus according to claim 13, further comprising a portion to be attached to a support.

16. The blood circuit detaching apparatus according to claim 13, further comprising an upper side and a lower side, with said dialyzer side clamping mechanism provided at said upper side, said patient side clamping mechanism provided at said lower side, and said cutting mechanism provided between said upper side and said lower side.

17. The blood circuit detaching apparatus according to claim 12, wherein said patient side clamping mechanism includes forceps members that are to clamp the patient-side part of the dialyzing artery plastic tube blood circuit and the patient-side part of the dialyzing vein plastic tube blood circuit.

18. The blood circuit detaching apparatus according to claim 17, further comprising a portion to be attached to a support.

19. The blood circuit detaching apparatus according to claim 17, further comprising an upper side and a lower side, with said dialyzer side clamping mechanism provided at said upper side, said patient side clamping mechanism provided at said lower side, and said cutting mechanism provided between said upper side and said lower side.

20. The blood circuit detaching apparatus according to claim 12, further comprising a portion to be attached to a support.

21. The blood circuit detaching apparatus according to claim 20, further comprising an upper side and a lower side, with said dialyzer side clamping mechanism provided at said upper side, said patient side clamping mechanism provided at said lower side, and said cutting mechanism provided between said upper side and said lower side.

22. The blood circuit detaching apparatus according to claim 12, further comprising an upper side and a lower side, with said dialyzer side clamping mechanism provided at said upper side, said patient side clamping mechanism provided at said lower side, and said cutting mehanism provided between said upper side and said lower side.

* * * * *